United States Patent [19]

Antane et al.

[11] Patent Number: 5,512,585

[45] Date of Patent: Apr. 30, 1996

[54] DIAMINOCYCLOBUTENE-3,4-DIONES

[75] Inventors: Madelene M. Antane, Lawrenceville; John A. Butera, Clarksburg; Bradford H. Hirth, Monmouth Junction; Schuyler A. Antane, Lawrenceville, all of N.J.

[73] Assignee: American Home Products Corporation, Madison, N.J.

[21] Appl. No.: 459,598

[22] Filed: Jun. 2, 1995

Related U.S. Application Data

[63] Continuation-in-part of Ser. No. 340,697, Nov. 16, 1994, Pat. No. 5,464,867.

[51] Int. Cl.$^6$ .................. A61K 31/44; C07D 213/36
[52] U.S. Cl. .................. 514/352; 514/344; 546/289; 546/309
[58] Field of Search .................. 546/289, 309; 514/344, 352

[56] References Cited

U.S. PATENT DOCUMENTS

| | | | |
|---|---|---|---|
| 4,390,701 | 6/1982 | Algieri et al. | 546/235 |
| 4,673,747 | 6/1987 | Nohara et al. | 546/334 |

FOREIGN PATENT DOCUMENTS

| | | | |
|---|---|---|---|
| 0426379 | 5/1991 | European Pat. Off. | 546/235 |

OTHER PUBLICATIONS

Grünefeld et al, Arch. Pharm., vol. 318, No. 12, Sect. (1985), pp. 1062–1070.
Takeno et al, Public Patent Disclosure Bull, No. 6–92915, Apr. 5, 1994.
Ehrhardt et al., Chem. Ber, 10:2506–2523 (1977).
Tietze et al, Chem. Ber, 124:1215–1221 (1991).
Tietze et al, Bioconjugate Chem. No. 2/3:148–153 (1991).
Neuse et al. Liebs. Ann. Chem. 4:619–632 (1973).

*Primary Examiner*—C. Warren Ivy
*Assistant Examiner*—Zima N. Davis
*Attorney, Agent, or Firm*—Richard K. Jackson

[57] ABSTRACT

The compound of the formula:

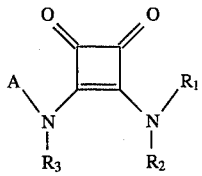

(I)

wherein:

$R_1$ and $R_2$ are, independent from each other, hydrogen, $C_{1-10}$ straight chain alkyl, $C_{1-10}$ branched alkyl, or $C_{3-10}$ cyclic or bicyclic alkyl;

$R_3$ is an acyl substituent selected from the group consisting of formyl, alkanoyl of 2 to 7 carbon atoms, alkenoyl of 3 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;

A is selected from the group consisting of:

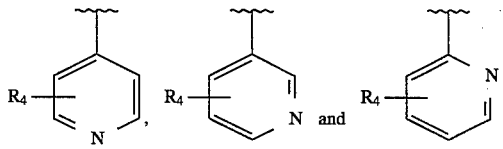

wherein:

$R_4$ is hydrogen, $C_{1-6}$ alkyl, $C_{1-6}$ perfluoroalkyl, $C_{1-6}$ alkoxy, $C_{1-6}$ perfluoroalkoxy, amino, $C_{1-6}$ alkylamino, $C_{2-12}$ dialkylamino, $C_{1-6}$ alkylsulfonamido, alkylcarboxamido containing 2 to 7 carbon atoms, nitro, cyano or carboxyl;

or a pharmaceutically acceptable salt thereof, are smooth muscle relaxants.

15 Claims, No Drawings

DIAMINOCYCLOBUTENE-3,4-DIONES

RELATED APPLICATIONS

This is a continuation-in-part of U.S. patent application Ser. No. 08/340,697, filed Nov. 16, 1994, now U.S. Pat. No. 5,464,876.

BACKGROUND OF INVENTION

The present invention relates to novel 1, 2-diamino derivatives of cyclobutene 3-4-diones having pharmacological activity, to a process for their preparation, to pharmaceutical compositions containing them, and to their use in the treatment of disorders associated with smooth muscle contraction; via potassium channel modulation. Such disorders include, but are not limited to: urinary incontinence, hypertension, asthma, premature labor, irritable bowel syndrome, congestive heart failure, angina, and cerebral vascular disease.

Stemp et al. disclose a class of amino substituted cyclobutenedione derivatives of chromans described as having blood pressure lowering activity and bronchodilatory activity in EP-426379-A2. Several series of 1-amino-2-phenylalkylamino-cyclobutene-3,4-diones are reported as H-2 receptor antagonists by Algieri et al. in U.S. Pat. No. 4,390,701. Several related 1-amino-2-phenoxyalkylamino derivatives are disclosed by Nohara et al. in U.S. Pat. No. 4,673,747.

The syntheses of variously substituted 1,2-diamino-cyclobutene-3,4-diones are described in the following publications: Tietze et al., *Chem Ber.* 1991, 124, 1215; Tietze et al., *Bioconjugate Chem.* 1991, 2, 148; Ehrhardt et al., *Chem. Ber.* 1977, 110, 2506, and Neuse et al., *Liebigs Ann. Chem.* 1973, 619. For example, Neuse et al. discloses 1-phenylamino-2-dimethylamino-cyclobut-1-ene-3,4-dione. The compounds of the present invention differ from the Neuse et al. compound in that they are N-acylated and they are useful as smooth muscle relaxants.

DESCRIPTION OF THE INVENTION

In accordance with the present invention, there is provided a group of compounds represented by the formula (I):

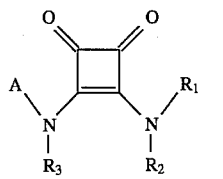

(I)

wherein:
$R_1$ and $R_2$ are, independent from each other, hydrogen, $C_{1-10}$ straight chain alkyl, $C_{1-10}$ branched alkyl, or $C_{3-10}$ cyclic or bicyclic alkyl;

$R_3$ is an acyl substituent selected from the group consisting of formyl, alkanoyl of 2 to 7 carbon atoms, alkenoyl of 3 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;

A is selected from the group consisting of:

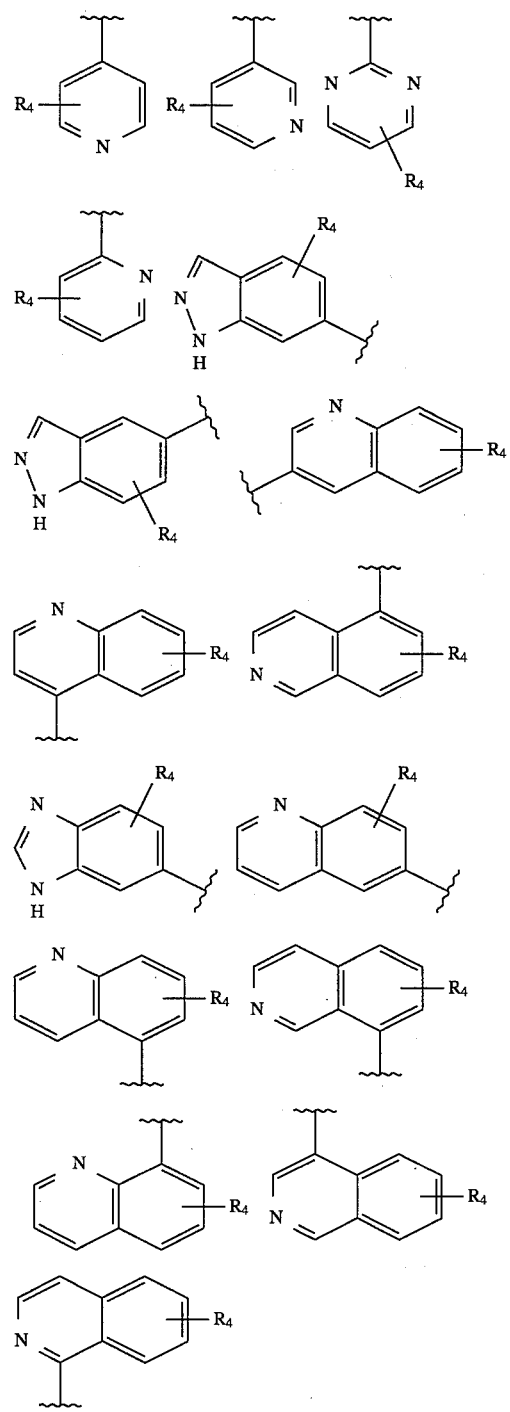

wherein:
$R_4$ is hydrogen, $C_{1-6}$ alkyl, $C_{1-6}$ perfluoroalkyl, $C_{1-6}$ alkoxy, $C_{1-6}$ perfluoroalkoxy, amino, $C_{1-6}$ alkylamino, $C_{2-12}$ dialkylamino, $C_{1-6}$ alkylsulfonamido, alkylcarboxamido containing 2 to 7 carbon atoms, nitro, cyano, carboxyl;

or, A is a substituted phenyl group of the following formula:

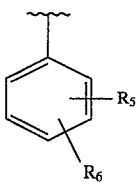

wherein:

$R_5$ and $R_6$, independent from each other, are selected from the following: cyano, nitro, amino, $C_{1-6}$ alkyl, $C_{1-6}$ perfluoroalkyl, $C_{1-6}$ alkoxy, $C_{1-6}$ perfluoroalkoxy, $C_{1-6}$ alkylamino, $C_{2-12}$ dialkylamino, sulfamyl, $C_{1-6}$ alkylsulfonamido, $C_{6-12}$ arylsulfonamido, alkylcarboxamido containing 2 to 7 carbon atoms, arylcarboxamido containing 7 to 13 carbon atoms, $C_{2-6}$ alkanoyl, $C_{1-6}$ alkylsulfonyl, $C_{1-6}$ perfluoroalkylsulfonyl, $C_{6-12}$ arylsulfonyl, chloro, bromo, fluoro, iodo, 1-imidazolyl, carboxyl or hydrogen;

or a pharmaceutically acceptable salt thereof.

A preferred aspect of this invention includes compounds of formula (I) wherein:

$R_1$ and $R_2$ are as stated above;

A is selected from the following:

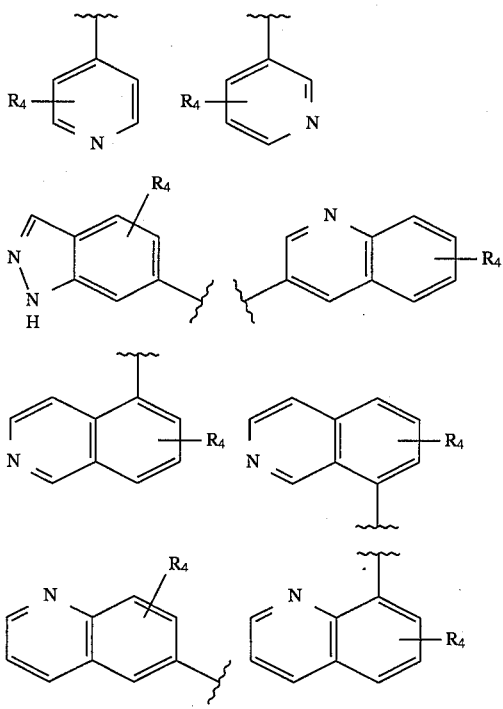

wherein:

$R_4$ is as stated above;

or, A is a substituted phenyl group of the following formula:

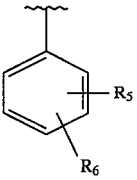

wherein:

$R_5$ and $R_6$, independent from each other, are selected from the following: cyano, nitro, amino, chloro, bromo, fluoro, iodo, 1-imidazolyl, alkyl of 1 to 6 carbon atoms, alkoxy of 1 to 6 carbon atoms, perfluoroalkyl of 1 to 6 carbon atoms, alkanoyl of 2 to 6 carbon atoms, carboxyl or hydrogen;

or a pharmaceutically acceptable salt thereof.

The most preferred aspect of this invention includes compounds of formula (I) wherein:

$R_1$ and $R_2$ are as stated above;

A is selected from the following:

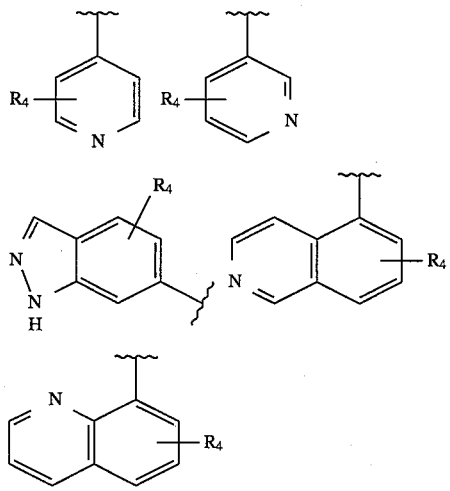

wherein:

$R_4$ is as stated above;

or, A is a substituted phenyl group of the following formula:

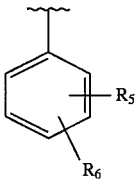

wherein:

$R_5$ and $R_6$, independent from each other, are selected from the following: cyano, nitro, amino, chloro, bromo, fluoro, iodo, 1-imidazolyl, alkyl of 1 to 6 carbon atoms, alkoxy of 1 to 6 carbon atoms, perfluoroalkyl of 1 to 6 carbon atoms, alkanoyl of 2 to 6 carbon atoms, carboxyl or hydrogen;

or a pharmaceutically acceptable salt thereof.

It is understood that the definition of the compounds of formula (I), when $R_1$, $R_2$, $R_3$, $R_4$, or $R_5$ contain asymmetric carbons, encompass all possible stereoisomers and mixtures thereof which possess the activity discussed below. In particular, it encompasses racemic modifications and any optical isomers which possess the indicated activity. Optical isomers may be obtained in pure form by standard separation techniques or enantiomer specific synthesis.. The compounds of this invention, throughout this specification, are equivalently name as 3,4-diones or 1,2-diones. The pharmaceutically acceptable salts of the basic compounds of this invention are those derived from such organic and inorganic acids as: lactic, citric, acetic, tartaric, succinic, maleic, malonic, hydrochloric, hydrobromic, phosphoric, nitric, sulfuric, methanesulfonic, and similarly known acceptable acids. Where $R_3$, $R_4$, or $R_5$ is a carboxyl group, salts of the compounds of this invention may be formed with bases such as alkali metals (Na, K, Li) or the alkaline earth metals (Ca or Mg).

The present invention also provides a process for the preparation of a compound of formula (I). More particularly, the compounds of formula (I) may be prepared by reacting a compound of formula (IIa):

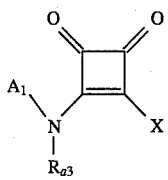
(IIa)

wherein X is a leaving group, for example, methoxy, ethoxy, isopropoxy, halogen or a similar leaving group and $A_1$ is A and $R_{a3}$ is $R_3$, as defined hereinbefore or a group of atoms convertible thereto, with a compound of formula (IV):

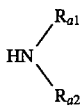
(IV)

wherein $R_{a1}$ and $R_{a2}$ are $R_1$ and $R_2$, respectively, as defined hereinbefore or a group of atoms convertible thereto and, where appropriate, converting $A_1$ into A or converting $R_{a1}$ into $R_1$ or converting $R_{a2}$ into $R_2$, followed by reacylation if necessary and, where desired, converting a compound having formula (I) into a pharmaceutically acceptable salt thereof or converting a salt of a compound having formula (I) into a compound having formula (I).

The compounds having formula (IIa) may be prepared by reaction of a compound of formula (II):

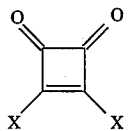
(II)

where X is as defined above with a compound of formula (III):

(III)

wherein $A_1$ is as defined above, followed by acylation to provide $R_{a3}$. Of course, acylation may also be conducted after reaction of the $A_1$ substituted compound with $HNR_{a1}R_{a2}$.

The reactions mentioned above may be carried out in a solvent such as acetonitrile, methanol or ethanol at elevated or ambient temperatures.

As mentioned previously, the compounds of formula (I) and their pharmaceutically acceptable salts have been found to relax smooth muscle. They are therefore useful in the treatment of disorders associated with smooth muscle contraction, disorders involving excessive smooth muscle contraction of the urinary tract (such as incontinence), or of the gastro-intestinal tract (such as irritable bowel syndrome), asthma, and hair loss. Furthermore, the compounds of formula (I) are active as potassium channel activators which render them useful for treatment of peripheral vascular disease, hypertension, congestive heart failure, stroke, anxiety, cerebral anoxia and other neurodegenerative disorders.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

The compositions are preferably adapted for oral administration. However, they may be adapted for other modes of administration, for example, parenteral administration for patients suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics and β-blocking agents.

The present invention further provides a compound of the invention for use as an active therapeutic substance. Compounds of formula (I) are of particular use in the induction of smooth muscle relaxation.

The present invention further provides a method of treating smooth muscle disorders in mammals including man, which comprises administering to the afflicted mammal an effective amount of a compound or a pharmaceutical composition of the invention.

The following examples are presented to illustrate rather than limit the methods for production of representative compounds of the invention.

EXAMPLE 1

N-(4-Cyano-phenyl)-N-[3,4-dioxo-2(1,2,2-trimethyl-propylamino)-cyclobut-1-enyl]-propionamide 4-Aminobenzonitrile (17.58 g, 149 mmol) was added to a solution of 3,4-diethoxy-3-cyclobutene-1,2-dione (25.31 g, 149 mmol) in absolute ethanol (450 mL). The mixture was heated at reflux overnight and the resulting suspension filtered hot to remove a small amount of a dirty yellow solid (discarded). The filtrate was gradually concentrated to afford several crops of 4-(3,4-dioxo-2-ethoxy-cyclobut-1-enylamino)-benzonitrile, as a bright yellow solid, which were collected by filtration and combined. Yield: 29.11 g (81%):

¹H NMR (DMSO-d₆): δ11.07 (s, 1H), 7.81 (d, 2H), 7.56 (d, 2H), 4.79 (q, 2H), 1.46 (t, 3H).

To the product of the preceding paragraph (13.00 g, 53.7 mmol) in ethanol (360 mL) was added 2-amino-3,3-dimethylbutane (7.2 mL, 54 mmol). The mixture was heated at reflux overnight. Gradual concentration of the reaction solution afforded two crops of 4-[3,4-dioxo-2-(1,2,2-trimethyl-propylamino)-cyclobut-1-enylamino]-benzonitrile, as a yellow precipitate, which were collected by filtration and combined. Yield: 11.34 g (71%); ¹H NMR (DMSO-d₆): δ9.89 (s, 1H), 7.78 (d, 2H), 7.72 (d, 1H), 7.60 (d, 2H), 3.96 (m, 1H), 1.18 (d, 3H), 0.91 (s, 9H To a solution of the product of preceding paragraph (1.20 g, 4.04 mmol) in N,N-dimethylformamide (36 mL) was added, in one portion, sodium hydride (as a 60% dispersion in mineral oil; 0.179 g, 4.48 mmol). The frothy suspension was stirred at room temperature for 15 minutes and then at 0° C. for an additional hour. Propionic anhydride (0.57 mL, 4.45 mmol) was added and the reaction mixture was stirred at 0° C. for 15 minutes and then allowed to warm to room temperature. After stirring overnight, the reaction mixture was concentrated. The resulting residue was taken up in methylene chloride and washed with aqueous sodium bicarbonate, brine and water. The organic layer was dried (Na₂SO₄) and concentrated. to afford a yellow foam which was purified by chromatography (CH₃OH/CH₂Cl₂) and trituration (Et₂O) to afford 0.68 g (48%) of N-(4-cyanophenyl)-N-[3,4-dioxo-2-(1,2,2-trimethyl-propylamino)-cyclobut- 1-enyl]-propionamide as a light yellow solid: mp 211°–214° C.; ¹H NMR (CDCl₃): δ 7.81 (d, 2H), 7.50–7.42 (m, 3H), 4.28 (m, 1H), 2.18 (m, 2H), 1.26 (d, 3H), 1.10 (t, 3H), 1.00 (s, 9H). IR (KBr): 3330, 2230, 1800, 1740, 1690, 1620 cm⁻¹; MS (m/z) 353 (M⁺).

Elemental analysis for $C_{20}H_{23}N_3O_3$ Calc'd: C, 67.97; H, 6.56; N, 11.89. Found: C, 67.77; H, 6.35; N, 11.87.

EXAMPLE 2

N-(4-Cyano-phenyl)-N-[3,4-dioxo-2-(1,2,2-trimethyl-propylamino)-cyclobut-1-enyl]-benzamide To a solution of the intermediate produced in Example 1, second paragraph (1.20 g, 4.04 mmol) in N,N-dimethylformamide (36 mL) was added, in one portion, sodium hydride (as a 60% dispersion in mineral oil; 0.178 g, 4.45 mmol). The frothy suspension was stirred at room temperature for 15 minutes and then at 0° C. for an additional hour. Benzoic anhydride (1.01 mL, 4.46 mmol) was added and the reaction mixture was stirred at 0° C. for 15 minutes and then allowed to warm to room temperature. After stirring overnight, the reaction mixture was concentrated. The resulting residue was taken up in methylene chloride and washed with aqueous sodium bicarbonate, brine and water. The organic layer was dried (Na₂SO₄) and concentrated to afford a yellow foam which was purified by chromatography (CH₃OH/CH₂Cl₂) and trituration (diethyl ether) to afford 0.71 g (44%) of product as a pale yellow solid: mp 229°–231° C.; ¹H NMR (CDCl₃): δ7.61–7.22 (m, 9H), 7.77 (d, 1H), 4.37 (m, 1H), 1.28 (d, 3H), 1.02 (s, 9H). IR (KBr): 3300, 2240, 1790, 1730, 1675, 1610 cm⁻¹; MS (m/z) 401 (M⁺).

Elemental analysis for $C_{24}H_{23}N_3O_3$ Calc'd: C, 71.80; H, 5.74; N, 10.47. Found: C, 71.49; H, 5.91; N, 10.18.

EXAMPLE 3

N-(4-Cyano-phenyl)-N-[3,4-dioxo-2-(1,2,2,-trimethyl-propylamino)-cyclobut-1-enyl]-methanesulfonamide To a solution of the intermediate of Example 1, second paragraph (1.20 g, 4.04 mmol) in N,N-dimethylformamide (36 mL) was added, in one portion, sodium hydride (as a 60% dispersion in mineral oil; 0.178 g, 4.45 mmol). The frothy suspension was stirred at room temperature for 15 minutes and then at 0° C. for an additional hour. Methanesulfonic anhydride (0.82 g, 4.71 mmol) was added and the reaction mixture was stirred at 0° C. for 15 minutes and then allowed to warm to room temperature. After stirring overnight, the reaction mixture was concentrated. The resulting residue was taken up in methylene chloride and washed with aqueous sodium bicarbonate, brine and water. The organic layer was dried (Na₂SO₄) and concentrated to afford a yellow foam which was purified by chromatography (CH₃OH/CH₂Cl₂) and trituration (diethyl ether) to afford 0.71 g (47%) of product as an off-white solid: mp 190°–191° C.; ¹H NMR (CDCl₃): δ7.79 (d, 2H), 7.54 (d, 2H), 6.77 (d, 1H), 4.29 (m, 1H), 3.24 (s, 3H), 1.24 (d, 3H), 0.96 (s, 9H). IR (KBr): 3350, 2220, 1800, 1725, 1610 cm⁻¹; MS (m/z) 375 (M⁺).

Elemental analysis for $C_{18}H_{21}N_3O_4S$ Calc'd: C, 57.58; H, 5.64; N, 11.19. Found: C, 57.60; H, 5.61; N, 11.10.

EXAMPLE 4

N-(4-Cyano-phenyl)-N-[3,4-dioxo-2-(1,2,2-trimethyl-propylamino)-cyclobut-1-enyl]-formamide To a solution of the intermediate of Example 1, second paragraph (1.20 g, 4.04 mmol) in N,N-dimethylformamide (36 mL) was added, in one portion, sodium hydride (as a 60% dispersion in mineral oil; 0.178 g, 4.45 mmol). The frothy suspension was stirred at roomtemperature for 15 minutes and then at 0° C. for an additional hour. Trifluoromethanesulfonic anhydride (0.75 mL, 4.46 mmol) was added and the reaction mixture was stirred at 0° C. for 15 minutes and then allowed to warm to room temperature. After stirring overnight, the reaction mixture was concentrated. The resulting residue was taken up in methylene chloride and washed with aqueous sodium bicarbonate and water. Recovered starting material, which precipitated as a yellow solid during workup, was filtered away. The organic layer was dried (Na₂SO₄) and concentrated to afford a brown residue which was purified by chromatography (CH₃OH/CH₂Cl₂), trituration (diethyl ether) and recrystallization (EtOAc/Hex) to afford 0.12 g (9%) of product as a light yellow solid: mp 187°–190° C.; ¹H NMR (CDCl₃): δ10.28 (s, 1H), 8.33 (s, 1H), 7.67 (d, 2H), 7.58 (d, 2H), 5.07 (m, 1H), 1.55 (d, 3H), 1.04 (s, 9H). IR (KBr): 3400, 2220, 1800, 1740, 1690, 1620 cm⁻¹; MS (m/z) 325 (M⁺).

Elemental analysis for $C_{18}H_{19}N_3O_3$ Calc'd: C, 66.44; H, 5.89; N, 12.91. Found: C, 66.29; H, 5.76; N, 12.74.

EXAMPLE 5

Hexanoic acid (4-cyano-phenyl)-[3,4-dioxo-2-(1,2,2-trimethyl-propylamino)-cyclobut-1-enyl]-amide To a suspension of the intermediate of Example 1, second paragraph (0.70 g, 2.35 mmol) in pyridine (9 mL) was added hexanoic anhydride (1.50 mL, 6.48 mmol). The mixture was stirred overnight, stripped free of solvent and diluted with diethyl ether. A yellow solid (recovered starting material) which remained undissolved was filtered away. The filtrate was concentrated, dissolved in methylene chloride and stirred vigorously in the presence of an equal volume of dilute aqueous sodium bicarbonate. After 30 minutes the organic layer was removed, dried (Na₂SO₄) and concentrated. The resulting yellow film was purified by chromatography (CH₃OH/CH₂Cl₂) to afford 0.43 g (46%) of product as a pale yellow solid: mp 51°–65° C.; ¹H NMR (CDCl₃): δ7.81 (d, 2H), 7.48–7.38 (m, 3H), 4.28 (m, 1H), 2,13 (m, 2H), 1.60 (m, 2H), 1.29–1.13 (m, 7H), 0.99 (s, 9H), 0.86 (t, 3H). IR (KBr): 3340, 2230, 1800, 1725, 1610 cm$^{-1}$; MS (m/z) 395 (M$^+$).

Elemental analysis for $C_{23}H_{29}N_3O_3$ Calc'd: C, 69.85; H, 7.39; N, 10.62. Found: C, 69.69; H, 7.35; N, 10.50.

EXAMPLE 6

N-(4-Cyano-phenyl)-N-[3,4-dioxo-2,-(1,2,2-trimethyl-propylamino)-cyclobut-1-enyl]-isobutyramide To a solution of iso-butyric anhydride (0.42 mL, 2.53 mmol) in pyridine (9 mL) was added the intermediate of Example 1, second paragraph (0.75 g, 2.52 mmol). After stirring overnight additional anhydride (3.8 mL, 22.9 mmol) was added and stirring was continued for a second day. The mixture was stripped free of solvent and diluted with diethyl ether. A yellow solid (recovered starting material) which remained undissolved was filtered away. The filtrate was concentrated and the resulting yellow oil was purified by chromatography (CH$_3$OH/CH$_2$Cl$_2$) and trituration (diethyl ether) to afford 0.47 g (51%) of product as a pale yellow solid: mp 175°–176° C.; $^1$H NMR (CDCl$_3$): δ7.81 (d, 2H), 7.47 (d, 2H), 7.42 (d, 1H), 4.28 (m, 1H), 2.52 (m, 1H), 1.27 (d, 3H), 1.10 (m, 6H), 1.00 (s, 9H). IR (KBr): 3330, 2230, 1800, 1730, 1680, 1610 cm$^{-1}$; MS (m/z) 367 (M$^+$).

Elemental analysis for $C_{21}H_{25}N_3O_3$ Calc'd: C, 68.64; H, 6.86; N, 11.44. Found: C, 68.34; H, 6.75; N, 11.26.

EXAMPLE 7

N-(4-Cyano-phenyl)-N-[3,4-dioxo-2-(1,2,2-trimethyl-propylamino)-cyclobut-1-enyl]-3-phenyl-acrylamide To a suspension of the intermediate of Example 1, second paragraph (0.50 g, 1.68 mmol) in pyridine (6 mL) was added cinnamic anhydride (0.94 g, 3.38 mmol). After stirring overnight, the mixture was concentrated. The resulting residue was taken up in methylene chloride and washed with aqueous sodium bicarbonate and water. The organic layer was dried (Na$_2$SO$_4$) and concentrated to afford a yellow gum which was purified by chromatography (CH$_3$OH/CH$_2$Cl$_2$) and trituration (diethyl ether) to afford 0.24 g (47%) of product as an off-white solid: mp 235°–237° C.; $^1$H NMR (CDCl$_3$): δ7.80–7.61 (m, 3H), 7.50–7.32 (m, 8H), 6.21 (d, 1H), 4.32 (m, 1H), 1.29 (d, 3H), 1.03 (s, 9H). IR (KBr): 3330, 2220, 1800, 1730, 1620, 1600 cm$^{-1}$; MS (m/z) 427 (M$^+$).

Elemental analysis for $C_{26}H_{25}N_3O_3 \cdot (0.06\ CH_2Cl_2) \cdot (0.13\ Et_2O)$ Calc'd: C, 72.19; H, 6.02; N, 9.50. Found: C, 72.23; H, 5.96; N, 9.58.

EXAMPLE 8

N-(4-Cyano-phenyl)-N-[3,4-dioxo-2-(1,2,2-trimethyl-propylamino)-cyclobut-1-enylamino]-carbamic acid ethyl ester To a stirred solution of trimethylacetic acid (0.38 g, 3.72 mmol) in tetrahydrofuran (5 mL) at 0° C. was added, in order, N,N-diisopropylethylamine (0.65 mL, 3.73 mmol) and (after 10 minutes) ethyl chloroformate (0.36 mL, 3.77 mmol). The resulting suspension of trimethylacetyl ethyl carbonate was stirred for 30 minutes before use in the following step.

To a solution of the intermediate of Example 1, second paragraph (1.00 g, 3.36 mmol) in N,N-dimethylformamide (30 mL) was added, in one portion, sodium hydride (as a 60% dispersion in mineral oil; 0.150 g, 3.75 mmol). The frothy suspension was stirred at room temperature for 15 minutes and at 0° C. for an additional hour. The mixed anhydride suspension prepared in the preceding paragraph was added all at once. After stirring at room temperature overnight, additional sodium hydride (0.134 g, 3.35 mmol) was added and stirring was continued for a second night. The reaction solution was concentrated and the resulting residue was taken up in methylene chloride and washed with aqueous sodium bicarbonate and water. Unreacted starting material, which precipitated as a yellow solid during workup, was filtered away. The organic layer was dried (Na$_2$SO$_4$) and concentrated to afford a brown gum which was purified by chromatography (CH$_3$OH/CH$_2$Cl$_2$) and trituration (diethyl ether) to afford 0.20 g (16%) of N-(4-cyano-phenyl)-N-[3,4-dioxo-2-(1,2,2-trimethyl-propylamino)-cyclobut-1-enyl]-carbamic acid ethyl ester as a white solid: mp 158°–159° C.; $^1$H NMR (DMSO-d$_6$): δ8.18 (d, 2H), 7.88 (d, 2H), 7.59 (d, 2H), 4.35–4.07 (m, 3H), 1.23 (t, 3H), 1.19 (d, 3H), 0.91 (s, 9H). IR (KBr): 3340, 2230, 1800, 1720, 1620 cm$^{-1}$; MS (m/z) 369 (M$^+$).

Elemental analysis for $C_{20}H_{23}N_3O_4$ Calc'd: C, 65.03; H, 6.28; N, 11.37. Found: C, 64.97; H, 6.19; N, 11.17.

EXAMPLE 9

N-(4,Cyano-phenyl)-N-[3,4-dioxo-2-(1,2,2-trimethyl-propylamino)-cyclobut-1-enyl]-acetamide The intermediate of Example 1, second paragraph (1.0 g, 3.36 mmol), acetic anhydride (0.95 mL, 10.0 mmol), and pyridine (10 mL) were mixed and allowed to stand at room temperature for 24 hours. The reaction mixture was filtered, and the solid was washed with ethyl acetate yielding 0.84 g (76%) of a yellow solid: mp 284°–286° C. (dec); $^1$H NMR (CDCl$_3$): δ7.82 (d, 2H), 7.47 (d, 2H), 7.38 (br d, 1H), 4.27 (dq, 1H), 2.02 (s, 3H), 1.25 (d, 3H), 0.99 (s, 9H). IR (KBr): 3358, 2978, 2236, 1804, 1739, 1685, 1614 cm$^{-1}$; MS (m/z) 339 (M$^+$).

Elemental analysis for $C_{19}H_{21}N_3O_3$ Calc'd: C, 67.24; H, 6.24; N, 12.38 Found: C, 67.15; H, 6.19; N, 12.38

EXAMPLE 10

(R)-(−)-N-(4-Cyano-phenyl)-N-[3,4-dioxo-2-(1,2,2-trimethyl-propylamino)-cyclobut-1-enyl]-acetamide 4-(3,4-Dioxo-2-ethoxy-cyclobut-1-enylamino)-benzonitrile (1 g, 4.1 mmol) and a solution of (R)-1,2,2-trimethyl-propylamine (8.2 mmol) in ethanol (50 mL) were stirred at room temperature for 24 hours. The resulting yellow slurry was filtered and rinsed with ethyl acetate to yield 0.92 g (75%) of (+)-(R)-4-[3,4-dioxo-2-(1,2,2-trimethyl-propylamino)-cyclobut-1-enylamino]-benzonitrile as a yellow solid: spectral data was identical to the product of Example 1, paragraph 2, except with $[\alpha]_D^{25}=+12°$ (DMSO, c 0.009).

(R)-(−)-N-(4-Cyano-phenyl)-N-[3,4-dioxo-2-(1,2,2-trimethyl-propylamino)-cyclobut-1-enyl]-acetamide was prepared according to the procedure described in Example 9. From the intermediate of the preceding paragraph (0.22g, 0.74 mmol) and acetic anhydride (0.21 mL, 2.2 mmol) in pyridine (2.2 mL) there was obtained 0.1 g (40%) of a yellow solid: spectral data was identical to the product of Example 9, except with $[\alpha]_D^{25}=-264°$ (DMSO, c 0.009).

EXAMPLE 11

N-(4-Cyano-phenyl)-N-[3,4-dioxo-2-isopropylamino-cyclobut-1-enyl]-acetamide 4-(3,4-Dioxo-2-ethoxy-cyclobut-1-enylamino)-benzonitrile (1 g, 4.1 mmol) and isopropylamine (5 g, 84.6 mmol) in acetonitrile (125 mL) were stirred at room temperature for 24 hours. The resulting yellow slurry was filtered to give 0.78 g (31%) of 4-[3,4-dioxo-2-isopropylamino)-cyclobut- 1-enylamino]-benzonitrile as a yellow solid: mp 290°–292° C. (dec); $^1$H NMR (DMSO-d$_6$): δ9.89 (br s, 1H), 7.77 (d overlapping a br d, 3H), 7.58 (d, 2H), 4.19 (m, 1H), 1.25 (d, 6H). IR (KBr): 3200, 3178, 2239, 1794, 1665, 1608, 1576, 1524 cm$^{-1}$; MS (m/z) 255 (M$^+$).

Elemental analysis for C$_{14}$H$_{13}$N$_3$O$_2$ Calc'd: C, 65.87; H, 5.13; N, 16.46 Found: C, 65.39; H, 4.92; N, 16.41

N-(4-Cyano-phenyl)-N-[3,4-dioxo-2-isopropylamino)-cyclobut-1-enyl]-acetamide was prepared according to the procedure described in Example 9. From the reactant of the preceding paragraph (0.15 g, 0.59 mmol) and acetic anhydride (0.28 mL, 2.9 mmol) in pyridine (1.8 mL) there was obtained 0.1 g (57%) of pale yellow crystals: mp 187°–188° C.; $^1$H NMR (CDCl$_3$): δ7.82 (d, 2H), 7.45 (d, 2H), 7.22 (br d, 1H), 4.57 (m, 1H), 2.00 (s, 3H), 1.33 (d, 6H). IR (KBr): 3339, 2980, 2239, 1760, 1734, 1695, 1620 cm$^{-1}$; MS (m/z) 297 (M$^+$).

Elemental analysis for C$_{16}$H$_{15}$N$_3$O$_3$ Calc'd: C, 64.64; H, 5.08; N, 14.13 Found: C, 64.32; H, 4.83; N, 14.13

EXAMPLE 12

N-{2-[Acetyl-(2,2,3,3,3-pentafluoro-propyl)-amino]-3,4-dioxo-cyclobut-1-enyl}-N-(4-cyano-phenyl)-acetamide 4-(3,4-Dioxo-2-ethoxy-cyclobut-1-enylamino)-benzonitrile (1 g, 4.1 mmol) and 2,2,3,3,3-pentafluoropropylamine (3 mL) in ethanol were refluxed for 24 hours. The reaction mixture was filtered and the resulting solid was triturated with diethyl ether to give 1.0 g (71%) of 4-[3,4-dioxo-2-(2,2,3,3,3-pentafluoro-propylamino)-cyclobut-1-enylamino]-benzonitrile as a yellow solid: mp 272°–275° C. (dec); $^1$H NMR (DMSO-d$_6$): δ10.15 (br s, 1H), 8.19 (br s, 1H), 7.81 (d, 2H), 7.79 (d, 2H), 4.54 (dt, 2H). IR (KBr): 3185, 2239, 1804, 1672, 1608, 1565, 1548 cm$^{-1}$; MS (m/z) 346 ([M+H]$^+$).

Elemental analysis for C$_{14}$H$_8$F$_5$N$_3$O$_2$ Calc'd: C, 48.71; H, 2.34; N, 12.17 Found: C, 48.89; H, 2.11; N, 12.21

The product of the preceding paragraph (0.13 g, 0.38 mmol), acetic anhydride (0.11 mL, 1.1 mmol), and pyridine (1.1 mL) were mixed and allowed to stand at room temperature for 24 hours. The reaction mixture was diluted with ethyl acetate, filtered, and concentrated under reduced pressure. The resulting residue was taken up in hot ethyl acetate and filtered hot. The solution was allowed to cool to room temperature and hexanes was added to aid in the crystallization. The solid was filtered, and rinsed sparingly with ethyl acetate to give 0.10 g (63%) of N-{2-[acetyl-(2,2,3,3,3-pentafluoro-propyl)-amino]-3,4-dioxo-cyclobut-1-enyl}-N-(4-cyano-phenyl)-acetamide as a pale yellow solid: mp 187°–195° C. (dec); $^1$H NMR (CDCl$_3$): δ7.83 (d, 2H), 7.53 (d, 2H), 4.82 (br m, 2H), 2.37 (s, 3H), 2.07 (s, 3H). IR (KBr): 3435, 2237, 1805, 1772, 1734, 1707, 1603 cm$^{-1}$; MS (m/z) 429 (M$^+$).

Elemental analysis for C$_{18}$H$_{12}$F$_5$N$_3$O$_4$ Calc'd: C, 50.36; H, 2.82; N, 9.79 Found: C, 50.62; H, 2.64; N, 9.86

EXAMPLE 13

N-(4-Cyano, phenyl)-N-[2-(1,2,dimethyl-propylamino)-3,4-dioxo-cyclobut-1-enyl]-acetamide This compound was prepared according to the procedure described in Example 11, first paragraph. 4-(3,4-Dioxo-2-ethoxy-cyclobut-1-enylamino)-benzonitrile (1 g, 4.1 mmol) and (+)-1,2-dimethylpropylamine (5 g, 57.4 mmol) in acetonitrile (125 mL) there was obtained after trituration with methanol 0.28 g (24%) of 4-[2-(1,2-dimethyl-propylamino)-3,4-dioxo-cyclobut-1-enylamino)-benzonitrile as a yellow solid: mp 222°–224° C.; $^1$H NMR (DMSO-d$_6$): δ9.89 (br s, 1H), 7.78 (d, 2H), 7.73 (d, 1H), 7.59 (d, 2H), 3.98 (m, 1H), 1.76 (m, 1H), 1.19 (d, 3H 3H), 0.89 (d, 3H). IR (KBr): 2980, 2240, 1799, 1660, 1600, 1565, 1525 cm$^{-1}$; MS (m/z) 283 (M$^+$).

Elemental analysis for C$_{16}$H$_{17}$N$_3$O$_2$ Calc'd: C, 67.83; H, 6.05; N, 14.83 Found: C, 67.32; H, 5.94; N, 14.91

N-(4-Cyano-phenyl)-N-[2-(1,2-dimethyl-propylamino)-3,4-dioxo-cyclobut-1enyl]-enyl]-acetamide was prepared according to the procedure described in Example 9. From the product of the preceding 2paragraph(0.27 g, 0.95 mmol) and acetic anhydride (0.27 mL, 2.9 mmol) in pyridine (2.9 mL) there was obtained. 0.17 g (55%) of white crystals: mp 258°–262° C. (dec); $^1$H NMR (CDCl$_3$): δ7.82 (d, 2H), 7.46 (d, 2H), 7.29 (br d, 1H), 4.30 (m, 1H), 2.02 (s, 3H), 1.81 (m, 1H), 1.27 (d, 3H), 1.00 (d, 3H), 0.99 (d, 3H). IR (KBr): 3337, 2967, 2228, 1804, 1739, 1685, 1620 cm$^{-1}$; MS (m/z) 325 (M$^+$).

Elemental analysis for C$_{18}$H$_{19}$N$_3$O$_3$ Calc'd: C, 66.45; H, 5.87; N, 12.91 Found: C, 66.48; H, 5.82; N, 12.79

EXAMPLE 14

N-(3-Cyano-phenyl)-N-[3,4-dioxo-2-(1,2,2-trimethyl-propylamino)-cyclobut-1-enyl]-acetamide 3-Aminobenzonitrile (2.06 g, 17.4 mmol) and 3,4-diethoxy-3-cyclobutene-1,2-dione (2.97 g, 17.5 mmol) in absolute ethanol (50 mL) was refluxed overnight. The reaction mixture was filtered hot, then allowed to cool to room temperature. The resulting precipitate was filtered to give 3.4 g of a yellow solid which was used without further purification. This yellow solid (1 g, 4.1 mmol) and 2-amino-3,3-dimethylbutane (2 g, 19.8 mmol) in acetonitrile (125 mL) were stirred at room temperature for 24 hours. The reaction mixture was filtered to give 0.66 g (54%) of 3-[3,4-dioxo-2-(1,2,2-trimethyl-propylamino)-cyclobut-1-enylamino]-benzonitrile as a pale yellow solid: mp 296°–298° C. (dec); $^1$H NMR (DMSO-d$_6$): δ9.79 (br s, 1H), 7.94 (br s, 1H), 7.67 (d, 1H), 7.64 (dm, 1H), 7.53 (t, 1H), 7.45 (dm, 1H), 1H), 1.17 (d, 3H), 0.91 (s, 9H). IR (KBr): 3193, 3148, 2974, 2228, 1793, 1673, 1582, 1544 cm$^{-1}$; MS (m/z) 297 (M$^+$).

Elemental analysis for C$_{17}$H$_{19}$N$_3$O$_2$ Calc'd: C, 68.67; H, 6.44; N, 14.13 Found: C, 68.73; H, 6.36; N, 14.04

N-(3-Cyano-phenyl)-N-[3,4-dioxo-2-(1,2,2-trimethyl-propylamino)-cyclobut-1-enyl]-acetamide was prepared according to the procedure described in Example 9. From the product of the preceding paragraph (0.18 g, 0.61 mmol) and acetic anhydride (0.28 mL, 3.0 mmol) in pyridine (1.8 mL) there was obtained 0.14 g (68%) of white crystals: mp 253°–254° C.; $^1$H NMR (CDCl$_3$): δ7.81 (dt, 1H), 7.69–7.58 (m, 3H), 7.41 (br d, 1H), 4.27 (m, 1H), 2.01 (s, 3H), 1.25 (d, 3H), 0.99 (s, 9H). IR (KBr): 3337, 2965, 2237, 1804, 1739, 1684, 1619 cm$^{-1}$; MS (m/z) 339 (M$^+$).

Elemental analysis for C$_{19}$H$_{21}$N$_3$O$_3$ Calc'd: C, 67.24; H, 6.24; N, 12.38 Found: C, 67.21; H, 6.20; N, 12.38

EXAMPLE 15

(R)-N-(4-Cyano-phenyl)-N-[2-(1-cyclohexyl-ethylamino)-3,4-dioxo-cyclobut-1-enyl]-acetamide (R)-4-[2-(1-Cyclohexyl-ethylamino)-3,4-dioxo-cyclobut-1-enylamino]-benzonitrile was prepared according to the procedure described in Example 10, first paragraph. From 4-(3,4-dioxo-2-ethoxy-cyclobut-1-enylamino)-benzonitrile (0.36 g, 1.5 mmol) and (R)-(–)-1-cyclohexylethylamine (0.29 mL, 1.95 mmol) in absolute ethanol (5 mL) there was obtained after trituration with hot methanol 0.31 g (64%)of a yellow solid: mp 275°–280° C. (dec); $^1$H NMR (DMSO-d$_6$): δ9.87 (br s, 1H), 7.78 (d, 2H), 7.72 (d, 1H), 7.59 (d, 2H), 3.96 (m, 1H), 1.78–1.66 (m, 4H), 1.62 (m, 1H), 1.34 (m, 1H), 1.24–0.90 (m including a doublet at δ1.20, 8H). IR (KBr): 3200, 2920, 2850, 2220, 1790, 1660, 1600, 1560, 1528 cm$^{-1}$; MS (m/z) 323 (M$^+$).

Elemental analysis for C$_{19}$H$_{21}$N$_3$O$_2$ Calc'd: C, 70.57; H, 6.55; N, 12.99 Found: C, 70.19; H, 6.60; N, 13.00

This compound was prepared according to the procedure described in Example 12, second paragraph. From the product of the preceding paragraph (0.33 g, 1.02 mmol) and acetic anhydride (0.29 mL, 3.06 mmol) in pyridine (3.1 mL) there was obtained 0.62 g (40%) of (R)-N-(4-cyano-phenyl)-N-[2-(1 -cyclohexyl-ethylamino)-3,4-dioxo-cyclobut-1-enyl]-acetamide as a yellow solid: mp 194°–198° C.; [α]$_D^{25}$=–150.96° (DMSO, c 0.0084); $^1$H NMR (CDCl$_3$): δ7.82 (d, 2H), 7.46 (d, 2H), 7.25 (br m, 1H), 4.28 (m, 1H), 2.02 (s, 3H), 1.87–0.94 (m including a doublet at δ1.27, 14H). IR (KBr): 3337, 2930, 2865, 2237, 1803, 1729, 1690, 1620 cm$^{-1}$; MS (m/z) 365 (M$^+$).

Elemental analysis for C$_{21}$H$_{23}$N$_3$O$_3$ Calc'd: C, 69.02; H, 6.34; N, 11.50 Found: C, 68.72; H, 6.10; N, 11.55

EXAMPLE 16

N-(2-Butylamino-3,4-dioxo-cyclobut-1-enyl)-N-(4-cyano-phenyl)-acetamide

4-[2-Butylamino-3,4-dioxo-cyclobut-1-enylamino)-benzonitrile was prepared according to the procedure described in Example 11, first paragraph. From 4-(3,4-dioxo-2-ethoxy-cyclobut-1 -enylamino)-benzonitrile (1 g, 4.1 mmol) and butylamine (3 g, 41.0 mmol) in acetonitrile (125 mL) there was obtained 0.64 g (58%) of a yellow solid: mp 256°–258° C. (dec); $^1$H NMR (DMSO-d$_6$): δ10.00 (br s, 1H), 7.81 (br s, 1H), 7.77 (d, 2H), 7.57 (d, 2H), 3.60 (br q, 2H), 1.55 (quintet, 2H), 1.34 (sextet, 2H), 0.90 (t, 3H). IR (KBr): 3240, 2980, 2240, 1800, 1670, 1625, cm$^{-1}$; MS (m/z) 269 (M$^+$).

Elemental analysis for C$_{15}$H$_{15}$N$_3$O$_2$ Calc'd: C, 66.90; H, 5.61; N, 15.60 Found: C, 66.23; H, 5.80; N, 15.54

N-(2-Butylamino-3,4-dioxo-cyclobut-1-enyl)-N-(4-cyano-phenyl)-acetamide was prepared according to the procedure described in Example 12, paragraph two. From the product of the preceding paragraph (0.16 g, 0.59 mmol) and acetic anhydride (0.28 mL, 2.96 mmol) in pyridine (1.8 mL) there was obtained 0.05 g (27%) of white solid: mp 194°–196° C.; $^1$H NMR (CDCl$_3$): δ7.82 (d, 2H), 7.45 (d, 2H), 7.34 (br m, 1H), 3.78 (q, 2H), 2.01 (s, 3H), 1.65 (quintet, 2H), 1.44 (sextet, 2H), 0.98 (t, 3H). IR (KBr): 3315, 2957, 2228, 1796, 1727, 1696, 1598 cm$^{-1}$; MS (m/z) 311 (M$^+$).

Elemental analysis for C$_{17}$H$_{17}$N$_3$O$_3$ Calc'd: C, 65.58; H, 5.50; N, 13.50 Found: C, 65.45; H, 5.63; N, 13.45

EXAMPLE 17

N-(endo)-[2-(Bicyclo[2.2.1]hept-2-ylamino)-3,4-dioxo-cyclobut-1-enyl]-N-(4-cyano-phenyl)-actetamide (endo)-4-[2-(Bicyclo[2.2.1]hept-2-ylamino)-3,4-dioxo-cyclobut-1-enylamino]-benzonitrile was prepared according to the procedure described in Example 11, first paragraph. From 4-(3,4-dioxo-2-ethoxy-cyclobut-1-enylamino)-benzonitrile (0.37 g, 1.5 mmol) and (±)-endo-2-aminonorbornane (0.17 g, 1.5 mmol) in acetonitrile (30 mL) there was obtained after trituration with diethyl ether 0.32 g (69%) of a yellow solid: mp 251°–252° C. (dec); $^1$H NMR (DMSO-d$_6$): δ9.88 (br s, 1H), 7.85 (d, 1H), 7.78 (d, 2H), 7.60 (d, 2H), 4.35 (m, 1H), 2.36 (m, 1H), 2.23 (m, 1H), 2.2 (m, 1H), 1.69–1.23 (m, 6H), 0.91 (m, 1H). IR (KBr): 3200, 2942, 2220, 1798, 1668, 1600, 1565, 1535 cm$^{-1}$; MS (m/z) 307 (M$^+$).

Elemental analysis for C$_{18}$H$_{17}$N$_3$O$_2$ Calc'd: C, 70.34; H, 5.57; N, 13.67 Found: C, 70.03; H, 5.38; N, 13.97

N-(endo)-[2-(Bicyclo[2.2.1]hept-2-ylamino)-3,4-dioxo-cyclobut-1-enyl]-N-(4-cyano-phenyl)-acetamide was prepared according to the procedure described in Example 9. From the product of the preceding paragraph (0.021 g, 0.068 mmol) and acetic anhydride (0.033 mL, 0.35 mmol) in pyridine (0.21 mL) there was obtained 0.014 g (59%) of pale yellow solid: mp 282°–285° C. (dec); $^1$H NMR (CDCl$_3$): δ7.82 (d, 2H), 7.45 (d, 2H), 7.51 (br d, 1H), 4.63 (m, 1H), 2.48 (m, 1H), 2.31 (m, 1H), 2.20 (m, 1H), 2.02 (s, 3H), 1.75–1.30 (m, 6H), 0.96 (m, 1H). IR (KBr): 3343, 2957, 2239, 1803, 1730, 1690, 1620 cm$^{-1}$; MS (m/z) 349 (M$^+$).

Elemental analysis for C$_{20}$H$_{19}$N$_3$O$_3$ Calc'd: C, 68.75; H, 5.48; N, 12.03 Found: C, 68.39; H, 5.39; N, 12.02

EXAMPLE 18

N-(2-tert-Butylamino-3,4-dioxo-cyclobut-1-enyl)-N-(isoquinolin-5-yl)-acetamide

5-Aminoisoquinoline (4.24 g, 29.4 mmol) and 3,4-diethoxy-3-cyclobutene-1,2-dione (5 g, 29.4 mmol) in absolute ethanol (100 mL) were refluxed overnight. The reaction mixture was filtered to give 2.3 g of a solid which was used without further purification. This solid (0.3 g, 1.12 mmol) in tert-butylamine (50 mL) was refluxed for 3 hours. The reaction mixture was concentrated and triturated with diethyl ether to give 0.12 g (39%) of 3-tert-Butylamino-4-(isoquinolin-5-ylamino)-cyclobut-3-ene-1,2-dione as a white solid 0.125 hydrate: mp 268°–270° C. (dec); $^1$H NMR (DMSO-d$_6$): δ9.75 (s, 1H), 9.35 (s, 1H), 8.62 (d, 1H), 8.19 (s, 1H), 8.01 (d, 1H), 7.88 (d, 1H), 7.80 (d, 1H), 7.68 (t, 1H), 1.47 (s, 9H). IR (KBr): 3200, 1785 1670, 1600 cm$^{-1}$; MS (m/z) 295 (M$^+$).

Elemental analysis for C$_{17}$H$_{17}$N$_3$O$_2$•0.125 H$_2$O Calc'd: C, 69.14; H, 5.80; N, 14.23 Found: C, 68.08; H, 5.78; N, 13.75

N-(2-tert-Butylamino-3,4-dioxo-cyclobut-1-enyl)-N-(isoquinolin-5-yl)-acetamide was prepared according to the procedure described in Example 12, second paragraph. From the product of the preceding paragraph (0.30 g, 1.0 mmol) and acetic anhydride (0.29 mL, 3.0 mmol) in pyridine (3 mL) there was obtained 0.18 g (53%) of off-white crystals: mp 210°–213° C.; $^1$H NMR (CDCl$_3$): δ 9.41 (s, 1H), 8.66 (d, 1H), 8.19 (m, 1H), 8.09 (br s, 1H), 7.81–7.72 (m, 2H), 7.59 (d, 1H), 1.89 (s, 1H), 1.56 (s, 9H). IR (KBr): 3304, 2965, 1793, 1679, 1588 cm$^{-1}$; MS (m/z) 337 (M$^+$).

Elemental analysis for C$_{19}$H$_{19}$N$_3$O$_3$ Calc'd: C, 67.64; H, 5.68; N, 12.46 Found: C, 67.38; H, 5.65; N, 12.41

EXAMPLE 19

N-(2-tert-Butylamino-3,4-dioxo-cyclobut-1-enyl)-N-(pyridin-3-yl)-acetamide

3-Aminopyridine (2.77 g, 29.4 mmol) and 3,4-diethoxy-3-cyclobutene-1,2-dione (5 g, 29.4 mmol) in absolute ethanol (150 mL) were refluxed for 18 hours. The reaction mixture was concentrated and chromatographed in hexanes/ethyl acetate (1/4) to give 3.15 g of a white solid. This solid (2.6 g, 11.9 mmol) in tert-butylamine (50 mL) was refluxed for 3 hours. The reaction mixture was concentrated and triturated with diethyl ether to give 1.05 g (36%) of 3-tert-butylamino-4-(pyridin-3-ylamino)-cyclobut-3-ene-1,2-dione as a white solid: nap 250°–252° C. (dec); $^1$H NMR (DMSO-d$_6$): δ8.57 (s, 1H), 8.23 (d, 1H), 7.96 (d, 1H), 7.37

(m, 1H), 1.43 (s, 9H). IR (KBr): 1790, 1685, 1600 cm$^{-1}$; MS (m/z) 245 (M$^+$).

Elemental analysis for $C_{13}H_{15}N_3O_2$ Calc'd: C, 63.66; H, 6.16; N, 17.13 Found: C, 63.28; H, 6.22; N, 17.07

N-(2-tert-Butylamino-3,4-dioxo-cyclobut-1-enyl)-N-(pyridin-3-yl)-acetamide was prepared according to the procedure described in Example 12, second paragraph. From the product of the preceding paragraph (0.20 g, 0.82 mmol) and acetic anhydride (0.23 mL, 2.5 mmol) in pyridine (2.5 mL) there was obtained 0.15 g (68%) of white crystals: mp 194°–195° C.; $^1$H NMR (CDCl$_3$): δ8.74 (d, 1H), 8.62 (s, 1H), 7.83 (br s, 1H), 7.70 (m, 1H), 7.47 (dd, 1H), 2.00 (s, 3H), 1.52 (s, 9H). IR (KBr): 435, 3298, 1799, 1741, 1685, 1598 cm$^{-1}$; MS (m/z) 288 ([M+H]$^+$).

Elemental analysis for $C_{15}H_{17}N_3O_3$ Calc'd: C, 62.71; H, 5.96; N, 14.62 Found: C, 62.78; H, 5.91; N, 14.67

EXAMPLE 20

N-[3,4-Dioxo-2-(1.2.2-trimethyl-propylamino)-cyclobut-1-enyl]-N-(2-methoxy-5-trifluoromethyl-phenyl)-acetamide 2-Methoxy-5-trifluoromethylaniline (5.62 g, 29.4 mmol) and 3,4-diethoxy-3-cyclobutene-1,2-dione (5 g, 29.4 mmol) in absolute ethanol (100 mL) were refluxed for 66 hours. The reaction mixture was filtered and the precipitate was chromatographed in methanol/methylene chloride to give 1.88 g of a yellow solid. This solid (1.0 g, 3.2 mmol) and 2-amino-3,3-dimethylbutane (0.43 mL, 3.2 mmol) in absolute ethanol (20 mL) were stirred at room temperature for 18 hours. The reaction mixture was concentrated and chromatographed with methylene chloride/methanol (96:4) to give 0.91 g (78%) of 3-ethoxy-4-(2-methoxy-5-trifluoromethyl-phenylamino)-cyclobut-3-ene-1,2-dione as a white solid: mp 143°–155° C.; $^1$H NMR (DMSO-d$_6$): δ9.36 (s, 1H), 8.24 (d, 1H), 8.19 (d, 1H), 7.35 (dd, 1H), 3.99 (s, 3H), 1.18 (d, 3H), 0.91 (s, 9H). IR (KBr): 3293, 2976, 1802, 1690, 1591, 1543 cm$^{-1}$; MS (m/z) 370 (M$^+$).

Elemental analysis for $C_{18}H_{21}F_3N_2O_3$ Calc'd: C, 58.37; H, 5.72; N, 7.56 Found: C, 57.98; H, 5.65; N, 7.27

N-[3,4-Dioxo-2-(1,2,2-trimethyl-propylamino)-cyclobut-1-enyl]-N-(2-methoxy-5-trifluoromethyl-phenyl)-acetamide was prepared according to the procedure described in Example 12, second paragraph. From the product of the preceding paragraph (0.20 g, 0.54 mmol) and acetic anhydride (0.15 mL, 1.6 mmol) in pyridine (1.6 mL) there was obtained 0..16 g (73%) of white crystals: mp 76°–79° C.; $^1$H NMR (CDCl$_3$) δ7.73 (dd, 1H), 7.53 (d, 1H), 7.38 (br d, 1H), 7.12 (d, 1H), 4.25 (m, 1H), 3.92 (s, 3H), 1.96 (s, 3H), 1.24 (d, 3H), 1.00 and 0.99 (two singlets, 9H). IR (KBr): 3326, 2974, 1799, 1715, 1609 cm$^{-1}$; MS (m/z) 412 (M$^+$).

Elemental analysis for $C_{20}H_{23}F_3N_2O_4$ Calc'd: C, 58.25; H, 5.62; N, 6.79 Found: C, 58.44; H, 5.85; N, 6.47

EXAMPLE 21

(endo)-N-[2-(Bicyclo[2.2.1]hept-2-ylamino)-3,4-dioxo-cyclobut-1-enyl]-N-(pyridin-4-yl)-acetamide 4-Aminopyridine (2.77 g, 29.4 mmol) and 3,4-diethoxy-3-cyclobutene-1,2-dione (5 g, 29.4 mmol) in absolute ethanol (100 mL) were refluxed for 4 hours. The reaction mixture was concentrated and chromatographed in ethyl acetate to give 0.63 g of a white solid. This solid (0.33 g, 1.5 mmol) and (+)-(endo)-2-aminonorbornane (0.17 g, 1.5 mmol) in acetonitrile (30 mL) was stirred at room temperature for 24 hours. The reaction mixture was filtered and triturated with diethyl ether to give 0.35 g (36%) of (±)-(endo)-3-(bicyclo[2.2.1]hept-2-ylamino)-4-(pyridin-4-ylamino)-cyclobut-3-ene-1,2-dione as a pale yellow solid 1.56 hydrate: mp 270°–277° C. (dec); $^1$H NMR (DMSO-d$_6$): δ9.81 (br s, 1H), 8.41 (d, 2H), 7.88 (d, 1H), 7.44 (d, 2H), 4.34 (m, 1H), 2.35 (m, 1H), 2.23 (m, 1H), 2.10 (m, 1H), 1.69–1.20 (m, 6H), 0.90 (m, 1H). IR (KBr): 3365, 2957, 1799, 1691, 1630, 1599, 1533 cm$^{-1}$; MS (m/z) 283 (M$^+$).

Elemental analysis for $C_{16}H_{17}N_3O_2$•1.56 H$_2$O Calc'd: C, 61.71; H, 6.51; N, 13.49 Found: C, 61.76; H, 6.37 N, 13.27

(endo)-N-[2-{Bicyclo[2.2.1]hept-2-ylamino)-3,4-dioxo-cyclobut-1-enyl] -N-(pyridin-4-yl)-acetamide was prepared according to the procedure described in Example 12, second paragraph. From the product of the preceding paragraph (0.17 g, 0.60 mmol) and acetic anhydride (0.28 mL, 3.0 mmol) in pyridine (1.8 mL) there was obtained 0.08 g (41%) of pale yellow solid: mp 192°–194° C.; $^1$H NMR (CDCl$_3$): δ 8.80 (dd, 2H), 7.49 (br d, 1H), 7.30 (dd, 2H), 4.63 (m, 1H), 2.48 (m, 1H), 2.30 (m, 1H), 2.19 (m, 1H), 2.06 (s, 3H), 1.75–1.30 (m, 6H), 0.97 (m, 1H). IR (KBr): 3348, 2954, 1799, 1735, 1696, 1621 cm$^{-1}$; MS (m/z) 325 ([M+H]$^+$).

Elemental analysis for $C_{18}H_{19}N_3O_3$ Calc'd: C, 66.45; H, 5.89; N, 12.91 Found: C, 66.02; H, 5.87; N, 12.66

EXAMPLE 22

N-(2-sec-Butylamino-3,4-dioxo-cyclobut-1-enyl)-N-(4-cyano-phenyl)-acetamide

4-[2-sec-Butylamino-3,4-dioxo-cyclobut-1-enylamino)-benzonitrile was prepared according to the procedure described in Example 11, first paragraph. From 4-(3,4-dioxo-2-ethoxy-cyclobut-1-enylamino)-benzonitrile (1 g, 4.1 mmol) and (±)-sec-butylamine (excess) in acetonitrile (125 mL) there was obtained 1.36 g of a yellow solid: mp 245°–247° C.; $^1$H NMR (DMSO-d$_6$): δ9.89 (br s, 1H), 7.78 (d, 2H), 7.73 (d, 1H), 7.58 (d, 2H), 4.01 (m, 1H), 1.65–1.46 (m 2H), 1.23 (d, 3H), 0.89 (t, 3H). IR (KBr): 3217, 3185, 3000, 2228, 1798, 1664, 1609, 1527 cm$^{-1}$; MS (m/z) 269 (M$^+$).

Elemental analysis for $C_{15}H_{15}N_3O_2$ Calc'd: C, 66.90; H, 5.61; N, 15.60 Found: C, 66.78; H, 5.43; N, 15.61

N-(2-sec-Butylamino-3,4-dioxo-cyclobut-1-enyl)-N-(4-cyano-phenyl)-acetamide was prepared according to the procedure described in Example 12, second paragraph. From the product of the preceding paragraph (0.16 g, 0.52 mmol) and acetic anhydride (0.28 mL, 2.96 mmol) in pyridine (1.8 mL) there was obtained 0.14 g (78%) of yellow crystals: mp 220°–225° C. (dec.); $^1$H NMR (CDCl$_3$): δ7.80 (d, 2H), 7.44 (d, 2H), 7.14 (br d, 1H), 4.36 (m, 1H), 2.00 (s, 3H), 1.71–1.53 (m, 2H), 1.30 (d, 3H), 0.98 (s, 3H). IR (KBr): 3348, 2978 2239, 1803, 1739, 1690, 1622 cm$^{-1}$; MS (m/z) 311 (M$^+$).

Elemental analysis for $C_{17}H_{17}N_3O_3$ Calc'd: C, 65.58; H, 5.50; N, 13.50 Found: C, 65.18; H, 5.31; N, 13.33

EXAMPLE 23

(R)-N-[3,4-Dioxo-2-(1,2,2-trimethyl-propylamino)-cyclobut-1-enyl]-N-(pyridin-3-yl)-acetamide 3-Aminopyridine (2.77 g, 29.4 mmol) and 3,4-diethoxy-3-cyclobutene-1,2-dione (5 g, 29.4 mmol)in acetonitrile (35 mL) were refluxed for 18 hours. The reaction mixture was concentrated and chromatographed with 2% methanol in ethyl acetate to give 2.65 g of a white solid. This solid (0.9 g, 4.1 mmol) was stirred in a solution of (R)-1,2,2-trimethyl-propylamine (8.2 mmol) and ethanol (50 mL) at room temperature for 24 hours. The reaction mixture was filtered and rinsed with ethyl acetate to give 0.77 g (68%) of (+)-(R)-3-(1,2,2-trimethyl-propylamino)-4-(pyridin-3-ylamino)-cyclobut-3-ene-1,2-dione as a white solid: mp 283°–285° C.; $[α]_D^{25}$=+2.04° (DMSO, c 0.0098); $^1$H NMR (DMSO-d$_6$): δ8.19 (brs, 1H), 8.57 (d, 1H), 8.22 (dd, 1H), 7.96 (dm, 1H), 7.66 (brd, 1H), 7.37 (dd, 1H), 3.98 (m, 1H), 1.17 (d, 3H), 0.91 (s, 9H). IR (KBr): 3200, 2960, 1790, 1655, 1570, 1455 cm$^{-1}$; MS (m/z) 273 (M$^+$).

Elemental analysis for C$_{15}$H$_{19}$N$_3$O$_2$ Calc'd: C, 65.91; H, 7.01; N, 15.37 Found: C, 65.88; H, 7.04; N, 15.56

The title compound was prepared according to the procedure described in Example 9. From the product of the preceding paragraph (0.20 g, 0.73 mmol) and acetic anhydride (0.21 mL, 2.2 mmol) in pyridine (2.2 mL) there was obtained 0.14 g (61%) of a 0.4 hydrate of the title compound as white crystals: mp 149°–151° C.; $^1$H NMR (CDCl$_3$): δ8.75 (dd, 1H), 8.63 (d, 1H), 7.71 (dm, 1H), 7.49 (dd, 1H), 7.42 (brd, 1H), 2.27 (m, 1H), 2.01 (s, 3H), 1.26 (d, 3H), 1.00 (s, 9H). IR (KBr): 3325, 2960, 1800, 1740, 1690, 1620 cm$^{-1}$; MS (m/z) 315 ([M+H]$^+$).

Elemental analysis for C$_{17}$H$_{21}$N$_3$O$_3$•0.4 H$_2$O Calc'd: C, 63.30; H, 6.81; N, 13.03 Found: C, 63.45; H, 6.71; N, 12.98

EXAMPLE 24

(R)-N-[3,4-Dioxo-2,-(1,2,2-trimethyl-propylamino)-cyclobut-1-enyl]-N-(pyridin-4-yl)-acetamide 4-Aminopyridine (8.27 g, 87.9 mmol) and 3,4-diethoxy-3-cyclobutene-1,2-dione (15 g, 88 mmol) in acetonitrile (51 mL) were refluxed for 18 hours. The reaction mixture was diluted with ethanol, filtered and concentrated. Chromatography with 2% methanol in ethyl acetate afforded 2.59 g of a white solid. This solid (0.9 g, 4.1 mmol) was stirred in a solution of (R)-1,2,2-trimethyl-propylamine (8.2 mmol) and ethanol (50 mL) at room temperature for 24 hours. The reaction mixture was filtered and rinsed with ethyl acetate to give 0.70 g (62%) of (+)-(R)-3-(1,2,2-trimethyl-propylamino)-4-(pyridin-4-ylamino)-cyclobut-3-ene-1,2-dione as a white solid: mp 275°–279° C. (dec); [α]$_D^{25}$=+6.02° (DMSO, c 0.0066); $^1$H NMR (DMSO-d$_6$): δ9.80 (s, 1H), 8.41 (dd, 2H), 7.73 (brd, 1H), 7.45 (dd, 2H), 3.97 (m, 1H), 1.17 (d, 3H), 0.91 (s, 9H). IR (KBr): 3210, 3160, 1800, 1670, 1610, 1530 cm$^{-1}$; MS (m/z) 273 (M$^+$).

Elemental analysis for C$_{15}$H$_{19}$N$_3$O$_2$ Calc'd: C, 65.91; H, 7.01; N, 15.37 Found: C, 65.80; H, 7.01; N, 15.60

The title compound was prepared according to the procedure described in Example 9. From the product of the preceding paragraph (0.20 g, 0.73 mmol) and acetic anhydride (0.21 mL, 2.2 mmol) in pyridine (2.2 mL) there was obtained 0.08 g (35%) of the title compound as a white solid: mp 140°–142° C. (dec); $^1$H NMR (CDCl$_3$): δ8.81 (dd, 2H), 7.32 (brd, 1H), 7.28 (dd, 2H), 4.27 (m, 1H), 2.05 (s, 3H), 1.25 (d, 3H), 0.99 (s, 9H). IR (KBr): 3340, 2980, 1790, 1720, 1690, 1610 cm$^{-1}$; MS (m/z) 315 ([M+H]$^+$).

Elemental analysis for C$_{17}$H$_{21}$N$_3$O$_3$ Calc'd: C, 64.74; H, 6.71; N, 13.32 Found.: C, 64.46; H, 6.68; N, 13.13

EXAMPLE 25

(R)-N-[3,4-Dioxo-2-(1,2,2-trimethyl-propylamino)-cyclobut-1-enyl]-3-methyl-N-(pyridin-4-yl)-butyramide This compound was prepared according to the procedure described in Example 9. From the product of the first paragraph of Example 24 (0.17 g, 0.62 mmol) and isovaleric anhydride (0.36 mL, 1.86 mmol) in pyridine (2.5 mL) there was obtained 0.08 g (36%) of the title compound as an off-white solid: mp 193°–196° C.; $^1$H NMR (CDCl$_3$): δ8.81 (dd, 2H), 7.36 (dm, 1H), 7.27 (dd, 2H), 4.28 (m, 1H), 2.20–2.02 (m, 3H), 1.26 (d, 3H), 0.99 (s, 9H), 0.90 (d, 3H), 0.89 (d, 3H). IR (KBr): 3310, 2950, 1795, 1720, 1700, 1610 cm$^{-1}$; MS (m/z) 357 ([M+H]$^+$).

Elemental analysis for C$_{20}$H$_{27}$N$_3$O$_3$ Calc'd: C, 67.20; H, 7.61; N, 11.76 Found: C, 66.71; H, 7.63; N, 11.63

EXAMPLE 26

(R)-(-)-N-[3,4-Dioxo-2-(1,2,2-trimethyl-propylamino)-cyclobut-1-enyl]-N-(pyridin-4-yl)-pentylamide This compound was prepared according to the procedure described in Example 9. From the product of the first paragraph of Example 24 (0.20 g, 0.73 mmol) and valeric anhydride (0.42 mL, 2.2 mmol) in pyridine (2.9 mL) there was obtained 0.17 g (65%) of the title compound as a pale yellow solid: mp 160°–165° C. (dec); [α]$_D^{25}$=−202.72° (DMSO, c 0.0076); $^1$H NMR (CDCl$_3$): δ8.81 (dd, 2H), 7.38 (dm, 1H), 7.28 (dd, 2H), 4.28 (m, 1H), 2.18 (dt, 2H), 1.59 (m, 2H), 1.31–1.20 (m, 2H), 1.26 (d, 3H), 1.00 (s, 9H), 0.8 (t, 3H). IR (KBr): 3310, 2970, 1795, 1720, 1700, 1610 cm$^{-1}$; MS (m/z) 357 ([M+H]$^+$).

Elemental analysis for C$_{20}$H$_{27}$N$_3$O$_3$ Calc'd: C, 67.20; H, 7.61; N, 11.76 Found: C, 66.93; H, 7.73; N, 11.84

The smooth muscle relaxing activity of the compounds of this invention was established in accordance with standard pharmaceutically accepted test procedures with representative compounds as follows:

Sprague-Dawley rats (150–200 g) are rendered. unconscious by CO$_2$ asphyxiation and then euthanized by cervical dislocation. The bladder is removed into warm (37 deg. C.) physiological salt solution (PSS) of the following composition (mM): NaCl, 118.4; KCl, 4.7; CaCl$_2$, 2.5; MgSO$_4$, 4.7; H$_2$O, 1.2; NaHCO$_3$, 24.9; KH$_2$PO$_4$, 1.2; glucose, 11.1; EDTA, 0.023; gassed with 95% O$_2$; 2/5% CO$_2$; pH 7.4. The bladder is opened and then cut into strips 1–2 mm in width and 7–10 mm in length. The strips are subsequently suspended in a 10 mL tissue bath under an initial resting tension of 1.5 g. The strips are held in place by two surgical clips one of which is attached to a fixed hook while the other is attached to an isometric force transducer. The preparations, which usually exhibit small spontaneous contractions, are allowed to recover for a period of 1 hour prior to a challenge with 0.1 uM carbachol. The carbachol is then washed out and the tissue allowed to relax to its resting level of activity. Following a further 30 min period of recovery an additional 15 mM KCl are introduced into the tissue bath. This increase in KCl concentration results in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle are introduced into the tissue bath. Contractile activity is measured for each compound or vehicle concentration during the last minute of a 30 minute challenge.

The isometric force developed by the bladder strips is measured using a concentration required to elicit 50% inhibition of pre-drug contractile activity (IC$_{50}$ concentration) is calculated from this concentration-response curve. The maximum percentage inhibition of contractile activity evoked by a test compound is also recorded for concentrations of test compound less than or equal to 30 μM.

The results of this study are shown in Table I.

TABLE I

| Inhibition of Contractions in Isolated Rat Bladder Strips | | |
| --- | --- | --- |
| Compound | n | IC$_{50}$ μM |
| Example 1 | 2 | 0.50 + 0.0 |

TABLE I-continued

Inhibition of Contractions in Isolated Rat Bladder Strips

| Compound | n | IC$_{50}$ μM |
|---|---|---|
| Example 2 | 2 | 0.29 ± 0.04 |
| Example 5 | 2 | 0.35 ± 0.1 |
| Example 6 | 4 | 0.57 ± 0.2 |
| Example 7 | 2 | 0.37 ± 0.08 |
| Example 9 | 4 | 0.23 ± 0.05 |
| Example 10 | 2 | 0.31 ± 0.05 |
| Example 11 | 2 | 9.7 ± 4.1 |
| Example 13 | 2 | 0.2 ± 0.1 |
| Example 14 | 2 | 3.2 ± 0.92 |
| Example 16 | 2 | 1.24 ± 0.54 |
| Example 17 | 2 | 1.84 ± 0.36 |
| Example 21 | 1 | 10.6 |
| Example 23 | 3 | 7.2 ± 1.6 |
| Example 24 | 2 | 2.5 ± 0.2 |
| Example 25 | 3 | 10.8 ± 1.6 |
| Example 26 | 4 | 4.9 ± 1.2 |

Hence, the compounds of this invention have a pronounced effect on smooth muscle contractility and are useful in the treatment of urinary incontinence, irritable bladder and bowel disease, asthma, hypertension, stroke, and similar diseases as mentioned above, which are amenable to treatment with potassium channel activating compounds by administration, orally, parenterally, or by aspiration to a patient in need thereof.

What is claimed is:

1. A compound of the formula:

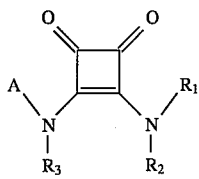
(I)

wherein:

$R_1$ and $R_2$ are, independent from each other, hydrogen, $C_{1-10}$ straight chain alkyl, $C_{1-10}$ branched alkyl, or $C_{3-10}$ cyclic or bicyclic alkyl;

$R_3$ is an acyl substituent selected from the group consisting of formyl, alkanoyl of 2 to 7 carbon atoms, alkenoyl of 3 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;

A is selected from the group consisting of:

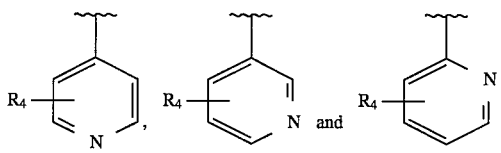

wherein:

$R_4$ is hydrogen, $C_{1-6}$ alkyl, $C_{1-6}$ perfluoroalkyl, $C_{1-6}$ alkoxy, $C_{1-6}$ perfluoroalkoxy, amino, $C_{1-6}$ alkylamino, $C_{2-12}$ dialkylamino, $C_{1-6}$ alkylsulfonamido, alkylcarboxamido containing 2 to 7 carbon atoms, nitro, cyano or carboxyl;

or a pharmaceutically acceptable salt thereof.

2. A compound of claim 1 which is N-(2-tert-butylamino-3,4-dioxo-cyclobut-1-enyl)-N-(pyridin-3-yl)-acetamide.

3. A compound of claim 1 which is (endo)-N-[2-(bicyclo[2.2.1]hept-2-ylamino)-3,4-dioxo-cyclobut-1-enyl]-N-(pyridin-4-yl)-acetamide.

4. A compound of claim 1 which is N-[3,4-Dioxo-2-(1,2,2-trimethyl-propylamino)-cyclobut-1-enyl]-N-(pyridin-3-yl)-acetamide.

5. A compound of claim 1 which is (R)-N-[3,4-Dioxo-2-(1,2,2-trimethyl-propylamino)-cyclobut-1-enyl]-N-(pyridin-3-yl)-acetamide.

6. A compound of claim 1 which is N-[3,4-Dioxo-2-(1,2,2-trimethyl-propylamino)-cyclobut-1-enyl]-N-(pyridin-4-yl)-acetamide.

7. A compound of claim 1 which is (R)-N-[3,4-Dioxo-2-(1,2,2-trimethyl-propylamino)-cyclobut-1-enyl]-N-(pyridin-4-yl)-acetamide.

8. A compound of claim 1 which is N-[3,4-Dioxo-2-(1,2,2-trimethyl-propylamino)-cyclobut-1-enyl]-3-methyl-N-(pyridin-4-yl)-butyramide.

9. A compound of claim 1 which is (R)-N-[3,4-Dioxo-2-(1,2,2-trimethyl-propylamino)-cyclobut-1-enyl]-3-methyl-N-(pyridin-4-yl)-butyramide.

10. A compound of claim 1 which is N-[3,4-Dioxo-2-(1,2,2-trimethyl-propylamino)-cyclobut-1-enyl]-N-(pyridin-4-yl)-pentylamide.

11. A compound of claim 1 which is (R)-(−)-N-[3,4-Dioxo-2-(1,2,2-trimethyl-propylamino)-cyclobut-1-enyl]-N-(pyridin-4-yl)-pentylamide.

12. A method for reducing the adverse effects of smooth muscle contractions which comprises administering, orally or parenterally, to a patient in need thereof, a compound of the formula:

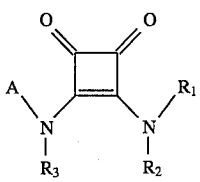
(I)

wherein:

$R_1$ and $R_2$ are, independent from each other, hydrogen, $C_{1-10}$ straight chain alkyl, $C_{1-10}$ branched alkyl, or $C_{3-10}$ cyclic or bicyclic alkyl;

$R_3$ is an acyl substituent selected from the group consisting of formyl, alkanoyl of 2 to 7 carbon atoms, alkenoyl of 3 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;

A is selected from the group consisting of:

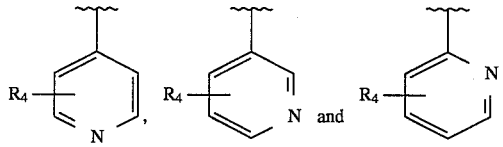

wherein:

$R_4$ is hydrogen, $C_{1-6}$ alkyl, $C_{1-6}$ perfluoroalkyl, $C_{1-6}$ alkoxy, $C_{1-6}$ perfluoroalkoxy, amino, $C_{1-6}$ alkylamino, $C_{2-12}$ dialkylamino, $C_{1-6}$ alkylsulfonamido, alkylcarboxmido containing 2 to 7 carbon atoms, nitro, cyano or carboxyl;

or a pharmaceutically acceptable salt thereof.

13. The method of claim 12 in which the smooth muscle adversely contracting causes urinary incontinence.

14. The method of claim 12 in which the smooth muscle adversely contracting causes irritable bowel syndrome.

15. A pharmaceutical composition comprising a compound as claimed in claim 1 in combination or association with a pharmaceutically acceptable carrier.

* * * * *